United States Patent
Zheng

(10) Patent No.: US 11,344,279 B2
(45) Date of Patent: May 31, 2022

(54) IMAGING METHOD FOR OBTAINING HUMAN SKELETON

(71) Applicant: Telefield Medical Imaging Limited, Hong Kong (HK)

(72) Inventor: Yongping Zheng, Hong Kong (HK)

(73) Assignee: Telefield Medical Imaging Limited, Hong Kong (HK)

( * ) Notice: Subject to any disclaimer, the term of this patent is extended or adjusted under 35 U.S.C. 154(b) by 94 days.

(21) Appl. No.: 16/629,579

(22) PCT Filed: Jul. 3, 2018

(86) PCT No.: PCT/CN2018/094310
§ 371 (c)(1),
(2) Date: Jan. 9, 2020

(87) PCT Pub. No.: WO2019/011159
PCT Pub. Date: Jan. 17, 2019

(65) Prior Publication Data
US 2021/0077064 A1    Mar. 18, 2021

(30) Foreign Application Priority Data

Jul. 11, 2017  (CN) .......................... 201710563512.2

(51) Int. Cl.
*A61B 8/00* (2006.01)
*A61B 8/08* (2006.01)

(52) U.S. Cl.
CPC .......... *A61B 8/0875* (2013.01); *A61B 8/4444* (2013.01); *A61B 8/4477* (2013.01);
(Continued)

(58) Field of Classification Search
CPC ... A61B 8/0875; A61B 8/4444; A61B 8/4477; A61B 8/466; A61B 8/483; A61B 8/5215;
(Continued)

(56) References Cited

U.S. PATENT DOCUMENTS 4,476,873 A * 10/1984 Sorenson ................. A61B 8/00
                                                               600/447
8,900,146 B2 * 12/2014 Zheng .................. A61B 8/4245
                                                               600/443
(Continued)

FOREIGN PATENT DOCUMENTS

CN    102497821 A      6/2012
CN    103417243 A     12/2013
JP    2015061592 A *   4/2015  ........... A61B 8/4209

OTHER PUBLICATIONS

Japanese to English Machine Translation of Kazuya Takagi's JP2015061592A (Year: 2015).*
(Continued)

*Primary Examiner* — Patricia J Park

(57) ABSTRACT

An imaging method for obtaining a human skeleton, comprising the following steps: S1. determining a target region and fixing an object to be scanned; S2. determining an imaging region; S3. scanning the target region to obtain a series of section images that record spatial position coordinates and scanning angle of the imaging probe; S4. determining the position of bones in a three-dimensional space according to the features reflected on the surfaces of the bones in the section images and the spatial position coordinates and scanning angle of the imaging probe, and obtaining position information of the bones; S6. continuously scanning the target region till the position information and section images of the bones in the skeleton in the entire target region are completely collected; and S7. displaying the skeleton in the three-dimensional space. By means of the method, the human skeleton structure can be obtained without radiation.

12 Claims, 5 Drawing Sheets

(52) U.S. Cl.
CPC .............. *A61B 8/466* (2013.01); *A61B 8/483* (2013.01); *A61B 8/5215* (2013.01)

(58) Field of Classification Search
CPC ... A61B 5/0095; A61B 8/4472; A61B 8/5207; A61B 8/4427; A61B 8/4245; A61B 8/085; A61B 8/00; A61B 8/5246; A61B 5/0033; A61B 5/0066; A61B 5/0073; A61B 5/0075; A61B 5/0097; A61B 5/0507

See application file for complete search history.

(56) References Cited

U.S. PATENT DOCUMENTS

| | | | |
|---|---|---|---|
| 9,123,148 B2 * | 9/2015 | Kyriakou | A61B 6/00 |
| 9,713,508 B2 * | 7/2017 | Schlenger | A61B 8/466 |
| 2012/0253181 A1 * | 10/2012 | Okamura | A61B 8/5238 |
| | | | 600/424 |
| 2016/0012582 A1 * | 1/2016 | Mauldin, Jr. | G06T 11/60 |
| | | | 382/131 |
| 2017/0079828 A1 * | 3/2017 | Pedtke | G05B 19/4099 |

OTHER PUBLICATIONS

International Search Report of PCT Patent Application No. PCT/CN2018/094310 dated Sep. 29, 2018.

* cited by examiner

IMAGING METHOD FOR OBTAINING HUMAN SKELETON

TECHNICAL FIELD

The present application relates to the technical field of image processing, in particular to an imaging method for obtaining a human skeleton.

BACKGROUND

In the prior art, the 3D human skeleton is usually obtained by X-ray or CT imaging when the human object is lying down. In the process of imaging, people will absorb some harmful radiation such as X-ray, so there is a potential risk. At the same time, the human body needs to be scanned while lying down, thus the three-dimensional human skeleton scanned will be different from the skeleton shape when standing. In addition, because the CT equipment must be installed and used in a special room to avoid radiation leakage, the multi plane X-ray imaging EOS system can obtain two orthogonal two-dimensional images when the human body is standing through a relatively low X-ray dose, that is, two orthogonal images in the front-rear direction and left-right direction of the human body, and then process the images through software, and combine with the normal spine skeleton model to obtain The 3D image of spine is obtained, but the 3D skeleton obtained by this method contains the part estimated by software, and the measurement results are not completely accurate. Moreover, although the radiation amount of this method is relatively small, there is still a harmful effect of radiation on human body, and it needs to be installed in a special radiation shielding room.

Therefore, how to get the three-dimensional skeleton of human body accurately and avoid the hazard caused by the radiation of detection method has become an urgent problem in the field.

SUMMARY

The application aims to solve the problem that the existing skeleton detection method is not accurate enough and may cause certain radiation hazard to human body, and provides an imaging method for obtaining the skeleton of human body, which uses a three-dimensional ultrasonic system to obtain the skeleton of detection body, has no radiation hazard and is convenient and easy to use.

The technical scheme of the present application for solving the above technical problems is as follows, providing an imaging method for obtaining a human skeleton, the skeleton comprising bones, wherein, comprising the following steps:

S1. determining a target region and fixing an object to be scanned;

S2. determining an imaging region by using a spatial sensor;

S3. scanning the target region by using an imaging probe to obtain a series of section images that record spatial position coordinates and scanning angle of the imaging probe;

S4. determining the position of bones in a three-dimensional space according to the features reflected on the surfaces of the bones in the section images and the spatial position coordinates and scanning angle of the imaging probe, and obtaining position information of the bones;

S6. continuously scanning the target region till the position information and section images of the bones in the skeleton in the entire target region are completely collected; and S7. displaying the skeleton in the three-dimensional space.

Preferably, the imaging method further comprises the following steps between steps S4 and S6:

S5. extracting the position information of the bones in a section image, and using the position information of the bones to detect the position information of the bones in the adjacent section image.

Preferably, the step S3 further comprises:

S3.1 enhancing the section images obtained by scanning the same bone position from different angles by image processing, which includes averaging, median filtering, or strongest signal selection.

Preferably, the step S3 further comprises:

S3.2 in the same bone position, through the imaging probe, acquiring multiple images by using different ultrasonic frequencies or combination of multiple probes, and enhancing the reflection of the surfaces of the bones through image processing method, wherein the image processing includes averaging, median filtering, or strongest signal selection.

Preferably, after the step S4, the imaging method further comprises:

S4.2 displaying the section images in real time.

Preferably, after the step S4, the imaging method further comprises:

S4.3 according to the section images and the position information of the bones, displaying the bones in three-dimensional space in real time.

Preferably, when the target region contains multiple target sub regions on different parts of the human body or different target sub regions on the same part of the human body, the imaging method further comprises the following steps:

S8. using pause command to pause data collection of the target sub region;

S9. using pause cancel command to continue to collect data in another target sub region through steps S1-S7.

Preferably, the imaging probe scans the target region in different directions and angles.

Preferably, when the target region contains multiple target sub regions on different parts of the human body, the imaging method further comprises the following steps after step S1:

S1.1 installing micro spatial positioning devices on different parts of the human body where the target sub regions to be detected is located.

Preferably, the step S7 further comprises:

Sa. displaying a standard skeleton model corresponding to the target region in real time; or Sb. according to the spatial position coordinates and scanning angle of the imaging probe, displaying position of the imaging probe relative to the standard skeleton model in real time during the scanning process; or Sc. adjusting the standard skeleton model according to the obtained position information of the bones to display a 3D skeleton model;

the standard skeleton model is a standard skeleton model of a normal human body, and the three-dimensional skeleton model is a skeleton model generated by simulating the standard skeleton model through the bone position information of the bones.

Preferably, the imaging method is one of ultrasonic imaging, photoacoustic imaging, terahertz imaging, infrared imaging and optical tomographic imaging.

Preferably, the skeleton includes spine bone, thorax, rib, pelvis and bones of four limbs.

Preferably, the scanning of the imaging probe is carried out manually, semi automatically or by a mechanical device.

BENEFICIAL EFFECT

The application provides an imaging method for obtaining a human skeleton, which uses a three-dimensional ultrasonic system to obtain the skeleton of detection body, has no radiation hazard and is convenient and easy to use.

BRIEF DESCRIPTION OF THE DRAWINGS

The application will be further described in combination with the accompanying drawings and embodiments, in which.

DETAILED DESCRIPTION OF THE PREFERRED EMBODIMENT

In order to enable those skilled in the art to understand the application more clearly, the application will be described in further detail below in combination with the drawings and specific embodiments.

The application discloses an imaging method for obtaining human skeleton, which is one of ultrasonic imaging, photoacoustic imaging, terahertz (THz) imaging, infrared imaging and optical tomography (OCT). The figure of the application takes the human spine bone as an example, but it does not mean that the human skeleton in the application only includes the human spine bone. In fact, the human skeleton in the application includes the human skeleton parts such as the spine bone, the thorax, the ribs, the pelvis, and the bones of the limbs, which are not limited here. The scanning of the imaging probe mentioned in the application can be carried out manually or by semi-automatic or mechanical device, and is not limited here.

Figure 1:
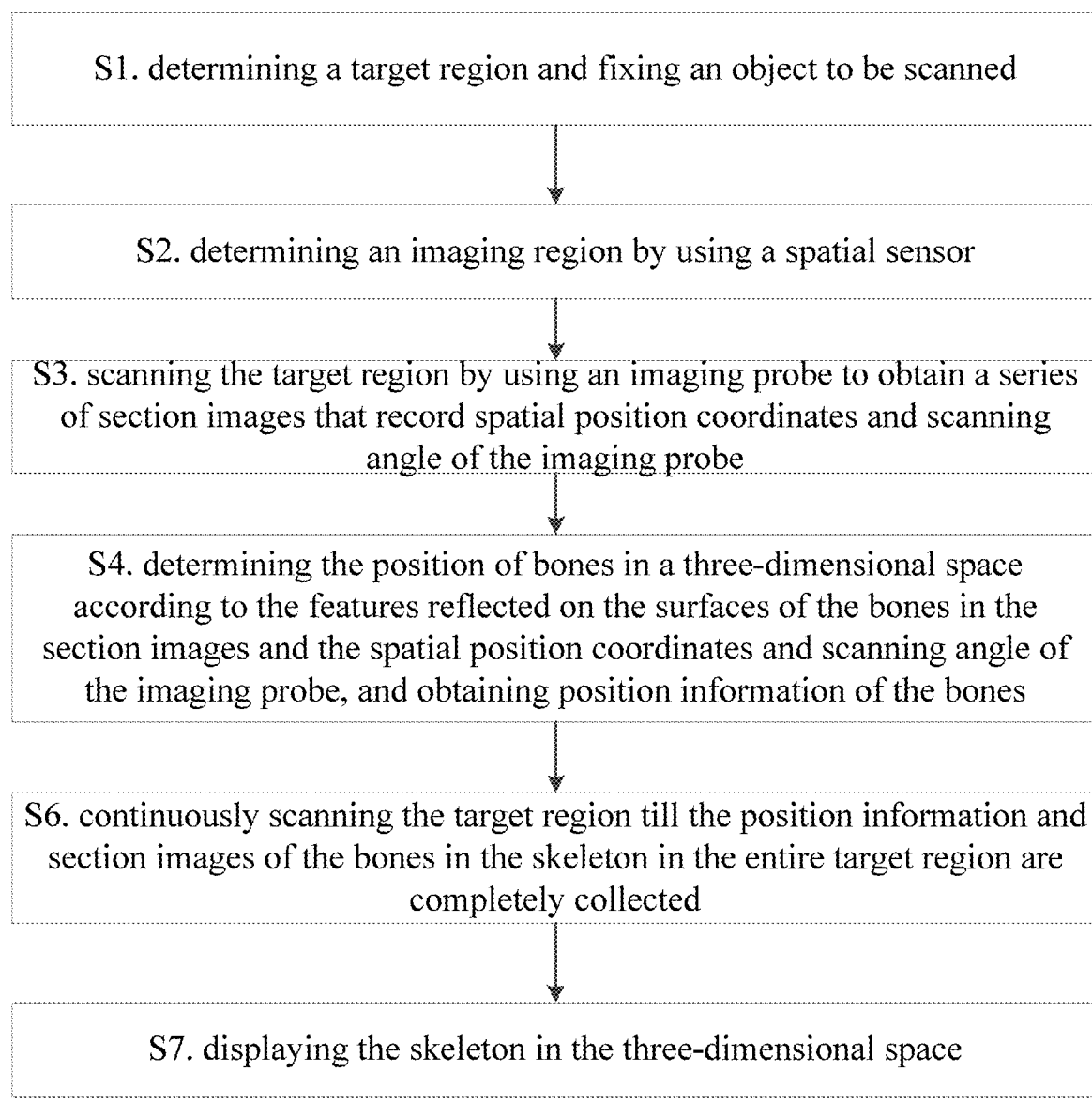
FIG. 1 is a flow chart of an imaging method for obtaining a human skeleton of the present application.

The main steps S1-S7 are shown in FIG. 1, determining a target region and fixing an object to be scanned (step S1). The target region is the imaging part or region to be detected, which can be a single region, multiple continuous regions and multiple separated regions. The object to be scanned can be various parts of the human body, and there is no restriction here.

Determining an imaging region by using a space sensor (step S2). The imaging region may include a single or multiple target regions. The space sensor is used to monitor the spatial position coordinates and scanning direction of the probe in real time. In the embodiment, the space sensor is directly loaded on the movable imaging probe, and in other embodiments of the application, the space sensor can also be loaded on other components moving together with the imaging probe, without limitation here.

Figure 2:
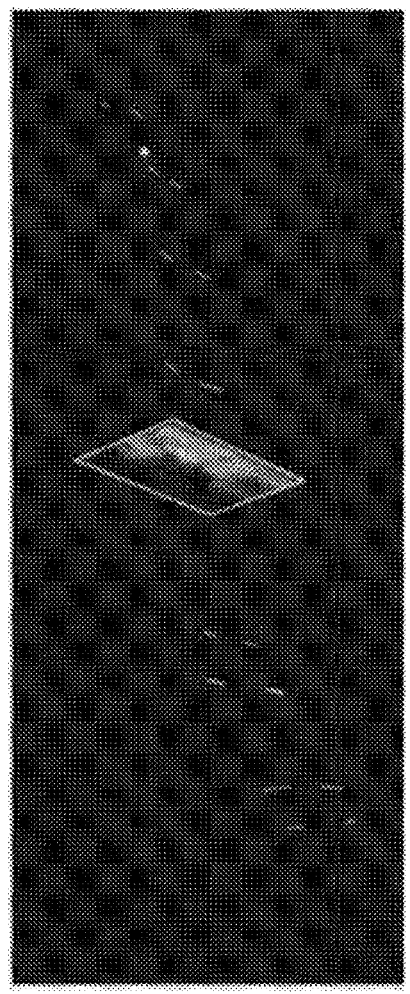
FIG. 2 is a section image of a preferred embodiment of the present application.

Scanning the target region by using an imaging probe to obtain a series of section images that record spatial position coordinates and scanning angle of the imaging probe (step S3). In a preferred embodiment of the application, a single section image is shown in FIG. 2. The acquisition data of step S3 includes the section image of ultrasonic scanning and the spatial position data of imaging probe obtained by the space sensor, that is, the spatial position coordinates and scanning angle of imaging probe. The data acquisition process is completed by the imaging probe, the space sensor and the central control module in real time. Specifically, the space sensor is connected with the imaging probe for obtaining the spatial position data of the imaging probe; the central control module is connected with the space sensor and the imaging probe for data and image processing and display. In the scanning process, the imaging probe can flexibly scan the same target area from different directions and angles until obtaining a clear section image, or the section image obtained by scanning the position of the same bone from different angles can be processed by image processing to enhance the reflection of bone surface, which includes averaging, median filtering, or strongest signal selection (step s3.1), so as to obtain clear bone surface features. It can be understood that in the position of the same bone, the imaging probe can use different ultrasonic frequencies, or the combination of multiple probes to obtain multiple images. Through image processing, the reflection of bone surface can be enhanced. Among them, image processing includes averaging, median filtering or the selection of the strongest signal (step s3.2), so as to facilitate the processing of cross-section image in the subsequent steps. Among them, the above scanning for the same part can be either manual scanning or mechanical scanning. For example, if the robot is used for scanning, the robot can scan 360 degrees around the target part to obtain section images of various directions and angles. The specific scanning method is not limited here.

Determining the position of bones in a three-dimensional space according to the features reflected on the surfaces of the bones in the section images and the spatial position coordinates and scanning angle of the imaging probe, and obtaining position information of the bones (step S4). The feature can be a feature point, a feature line or a feature surface, and the selection of the feature can be manually selected or automatically detected by an algorithm, such as automatically detecting the point with the highest brightness, etc. In addition to the reflection signal of bone surface, the above feature points, feature lines or feature surfaces can also be judged according to the shadow formed by bone in ultrasonic image. That is to say, the position of bone in three-dimensional space can be determined according to the reflection signal of bone surface and the shadow formed by bone in ultrasonic image. Because the spatial position coordinates and scanning angle information of the probe have been measured in step S3, the position information of the bone in the three-dimensional space can be determined, that is, the three-dimensional position coordinates of the bone.

Figure 3:
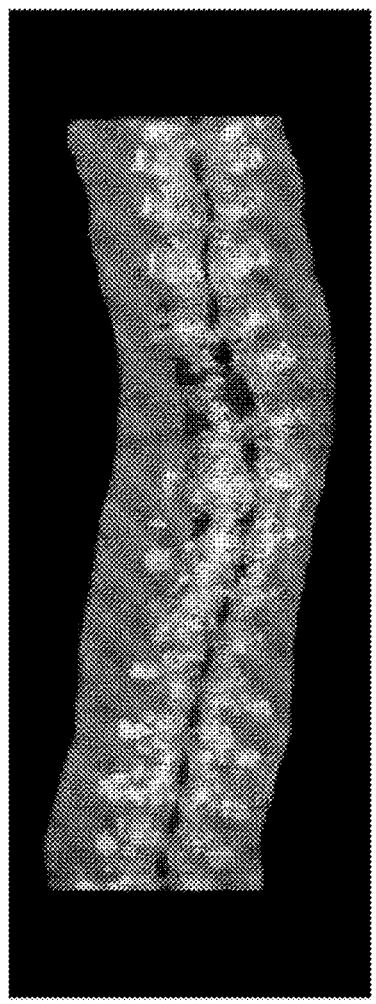
FIG. 3 is a coronal section image of a skeleton of a target region in a preferred embodiment of the present application.
Figure 4:
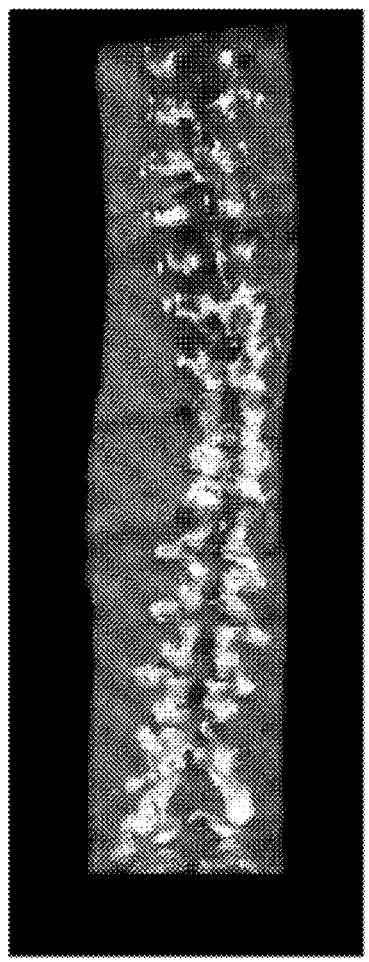
FIG. 4 is a three-dimensional image of the skeleton of the target region in a preferred embodiment of the present application.

Continuously scanning the target region till the position information and section images of the bones in the skeleton in the entire target region are completely collected (step S6). In a preferred embodiment of the application, as shown in FIG. 3, the section image of the skeleton of the target region collected by the imaging probe can further project the reflection signal of the obtained bone surface in all directions in the three-dimensional space, so as to obtain the similar effect of X-ray projection. Then, displaying the skeleton in the three-dimensional space (step S7). As shown in FIG. 4, a three-dimensional image of the skeleton of the target region is displayed. It can be understood that step S7 can further include displaying standard skeleton model, three-dimensional skeleton model and other information, and the specific details will be described in the following sections.

In order to improve the quality of the section image more efficiently, in the scanning process of imaging probe in different directions and angles, it is further included extracting the position information of the bones in a section image, and using the position information of the bones to detect the position information of the bones in the adjacent section image (step S5). When the position of the bone surface on a section image is determined, the ultrasonic imaging device will automatically adjust the focus depth to the depth of the bone surface. Therefore, when obtaining the next adjacent section image, the adjusted focus depth will be directly used, and so on, so that the focus is faster and the process of detecting and collecting data is more efficient. When the focus depth is determined, the depth related ultrasound signal amplification (TGC) will also be adjusted accordingly, so that the brightness of the image above or below the bone surface will be reduced correspondingly, so that the reflected signal on the bone surface is more obvious, the efficiency of data acquisition is increased, and the clearer section image can be obtained at the same time.

When the quality of the section image collected in step S3 is not good enough for analysis to obtain the position information of the bones, that is to say, in step S4, the position of the bones in the three-dimensional space cannot be determined through the characteristics reflected by the bone surface in the section image, after step S4, the imaging method of the application further includes:

S4.1 performing image processing on the section image, which includes image processing for brightness, contrast, noise and smoothness.

It can be understood that in the scanning process, the central control module can display the section image obtained in real time or the bone in the three-dimensional space, such as the three-dimensional image of the skeleton of the currently scanned target region (as shown in FIG. 4), or the bone can be displayed in the three-dimensional space after the scanning of the complete target region, which is not limited here. When it is necessary for the central control module to display the section image obtained during scanning or display the bone in three-dimensional space, after step S4, the method further includes the following steps:

Display the section image in real time (step S4.2). When the imaging probe scans at different positions and orientations, the image displayed on the screen will move and rotate accordingly, so that the operator can see the section image and the bone surface information in real time. According to the section image and the position information of the bones, as shown in FIG. 4, the bone is displayed in three-dimensional space in real time (S4.3). It can be understood that displaying bones in three-dimensional space can include displaying three-dimensional images of bones, and can include displaying three-dimensional models of bones, such as three-dimensional skeleton model and standard skeleton model, etc., details of which will be described in subsequent sections.

In the process of real-time display of bone in three-dimensional space in step S4.3, when the quality of section image collected in step S3 is not good enough for analysis to obtain bone position information, the imaging method of the application further includes between steps S4.2 and S4.3:

S4.2.1 performing image processing to the section image. The image processing includes image processing for brightness, contrast, noise and smoothness.

When the target region contains multiple target sub regions on different parts of the human body or different target sub regions on the same part of the human body, in order to make the above-mentioned ultrasonic scanning process fast and effective, and make the collected data all in the target region, so as to avoid the disadvantage of additional computation caused by collecting data outside the target region, the above-mentioned scanning process can be a segmented scanning process, that is, the method can further include the following steps:

S8. using pause command to pause data collection of the target sub region;

S9. using pause cancel command to continue to collect data in another target sub region through steps S1-S7.

That is to say, after scanning each target sub region and obtaining the position information of the bones of the target sub region through steps S1-S7, pause the data acquisition with the pause command; when the imaging probe is moved to another target sub region, give a pause cancel command to resume the image acquisition, so as to continue the acquisition of data in this target sub region. In this way, there is no need to scan the region outside the target region, that is, the region of no interest, so as to improve the efficiency of data acquisition and processing. The pause command or pause cancel command can be a switch, a key or a voice command, etc.

The above scanning for multiple different target sub regions can be either manual scanning or mechanical scanning. For example, if the robot is used for scanning, the robot can scan 360 degrees around the target to obtain section images of various directions and angles. The specific scanning mode is not limited here.

In different positions of human body, the imaging probe can scan in different directions, or can scan in different directions repeatedly in the same place. For example, when scanning the thigh bone, the imaging direction can be perpendicular to the radial direction of the bone. For example, when scanning the rib, the imaging probe can scan along the rib direction. When scanning the spine, multi-directional repeated scanning can be used to increase the clarity of the image.

When the target region contains multiple target sub regions of the human body in different parts, the imaging method further includes installing a micro spatial positioning device (step 1.1) on different human body parts where the target sub regions to be detected are located, so as to know the movement of the human body in the scanning process, thus to correct the position information of the bones accordingly.

Figure 5:
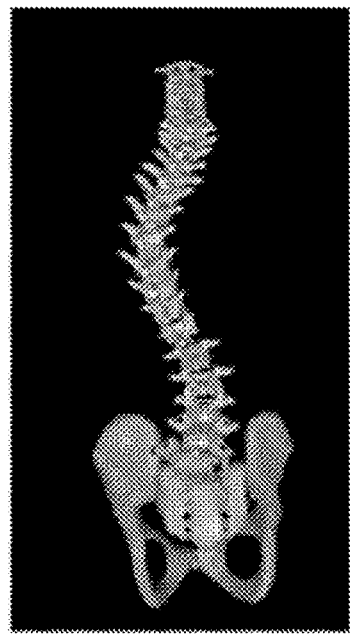
FIG. 5 is a three-dimensional skeleton model of the human body obtained by the application.

Furthermore, the standard skeleton model is stored in the central control module, which can be displayed in real time together with the section image or the three-dimensional image of the skeleton, or it can be fitted with the standard skeleton model by storing and processing the position information of the bones and other data collected in step S3 to generate the three-dimensional skeleton model. In the specification of the application, the standard skeleton model refers to the standard skeleton model of human body in healthy and normal conditions, and the three-dimensional skeleton model refers to the skeleton model generated by fitting the collected skeleton position information with the standard skeleton model. After steps S4.3 and S7, the standard skeleton model corresponding to the target region (step Sa) can also be displayed in real time, so that the operator can get a good reference in the scanning process. Furthermore, it can also include providing the position and angle information of the imaging probe according to the spatial sensor, and displaying the position of the imaging probe relative to the standard skeleton model in real time during the scanning process (step Sb). Further, the central control module adjusts the stored standard skeleton model according to the obtained position information of the bones in the skeleton to display the 3D skeleton model (step Sc), as shown in FIG. 5.

In conclusion, the application discloses an imaging method for obtaining the human skeleton, which can quickly and intuitively obtain the human skeleton structure without any radiation, thus avoiding the radiation hazard caused to the human body by X-ray detection and CT detection.

It should be understood that for those skilled in the art, improvements or transformations may be made according to the above description, and all of these improvements and transformations shall fall within the scope of protection of the appended claims of the application.

What is claimed is:

1. An imaging method for obtaining a human skeleton, the skeleton comprising bones, wherein, comprising following steps:
    S1. determining a target region and fixing an object to be scanned;
    S2. determining an imaging region by using a spatial sensor;
    S3. scanning the target region by using an imaging probe to obtain a series of section images that record spatial position coordinates and scanning angle of the imaging probe;
    S4. determining the position of bones in a three-dimensional space according to features reflected on surfaces of the bones in the section images and the spatial position coordinates and scanning angle of the imaging probe, and obtaining position information of the bones; the features comprise a feature point, a feature line or a feature surface, the position of bones in three-dimensional space is determined according to a shadow formed by bone in the section image;
    S6. continuously scanning the target region till the position information and section images of the bones in the skeleton in an entire target region are completely collected; and
    S7. displaying the skeleton in the three-dimensional space;
    the imaging method further comprises the following steps between steps S4 and S6:
    S5. extracting the position information of the bones in the section image, and using the position information of the bones to detect the position information of the bones in an adjacent section image; when the position information of the bones on the section image is determined, a focus depth of an ultrasonic imaging device is automatically adjusted to a depth of the bone;
    when obtaining the adjacent section image, the adjusted focus depth is directly used.

2. The imaging method for obtaining a human skeleton according to claim 1, wherein, step S3 further comprises:
    S3.1 enhancing the section images obtained by scanning the same bone position from different angles by image processing, which includes averaging, median filtering, or strongest signal selection.

3. The imaging method for obtaining a human skeleton according to claim 1, wherein, the step S3 further comprises:
    S3.2 in the same bone position, through the imaging probe, acquiring multiple images by using different ultrasonic frequencies or combination of multiple probes, and enhancing the reflection of the surfaces of the bones through image processing method, wherein the image processing includes average, median filtering or strongest signal selection.

4. The imaging method for obtaining a human skeleton according to claim 1, wherein, after step S4, the imaging method further comprises:
    S4.2 displaying the section images in real time.

5. The imaging method for obtaining a human skeleton according to claim 1, wherein, after step S4, the imaging method further comprises:
    S4.3 according to the section images and the position information of the bones, displaying the bones in three-dimensional space in real time.

6. The imaging method for obtaining a human skeleton according to claim 1, wherein, when the target region contains multiple target sub regions on different parts of a human body or different target sub regions on the same part of the human body, the imaging method further comprises the following steps:
    S8. using pause command to pause data collection of the target sub region;
    S9. using pause cancel command to continue to collect data in another target sub region through steps S1-S7.

7. The imaging method for obtaining a human skeleton according to claim 1, wherein, the imaging probe scans the target region in different directions and angles.

8. The imaging method for obtaining a human skeleton according to claim 1, wherein, when the target region contains multiple target sub regions on different parts of a human body, the imaging method further comprises the following steps after step S1:
    S1.1 installing micro spatial positioning devices on different parts of the human body where the target sub regions to be detected is located.

9. The imaging method for obtaining a human skeleton according to claim 1, wherein, step S7 further comprises:
    Sa. displaying a standard skeleton model corresponding to the target region in real time; or
    Sb. according to the spatial position coordinates and scanning angle of the imaging probe, displaying position of the imaging probe relative to the standard skeleton model in real time during a scanning process; or
    Sc. adjusting the standard skeleton model according to the obtained position information of the bones to display a 3D skeleton model;
    the standard skeleton model is a standard skeleton model of a normal human body, and a three-dimensional skeleton model is a skeleton model generated by simulating the standard skeleton model through the bone position information of the bones.

10. The imaging method for obtaining a human skeleton according to claim 1, wherein, the imaging method is one of ultrasonic imaging, photoacoustic imaging, terahertz imaging, infrared imaging, and optical tomographic imaging.

11. The imaging method for obtaining a human skeleton according to claim 1, wherein, the skeleton includes spine bone, thorax, rib, pelvis, and bones of four limbs.

12. The imaging method for obtaining a human skeleton according to claim 1, wherein, the scanning of the imaging probe is carried out manually, semi automatically or by a mechanical device.

\* \* \* \* \*